United States Patent
Türbachova

(10) Patent No.: US 9,017,972 B2
(45) Date of Patent: Apr. 28, 2015

(54) DNA METHYLATION ANALYSIS OF REGULATORY T CELLS THROUGH DNA-METHYLATION ANALYSIS OF THE TSDR REGION OF THE GENE FOXP3

(76) Inventor: Ivana Türbachova, Berlin (DE)

( * ) Notice: Subject to any disclaimer, the term of this patent is extended or adjusted under 35 U.S.C. 154(b) by 503 days.

(21) Appl. No.: 13/000,502

(22) PCT Filed: Jul. 2, 2009

(86) PCT No.: PCT/EP2009/004793
§ 371 (c)(1),
(2), (4) Date: Mar. 25, 2011

(87) PCT Pub. No.: WO2010/000474
PCT Pub. Date: Jan. 7, 2010

(65) Prior Publication Data
US 2011/0177505 A1    Jul. 21, 2011

(30) Foreign Application Priority Data

Jul. 3, 2008 (EP) .................................... 08012056

(51) Int. Cl.
| | | |
|---|---|---|
| C12Q 1/68 | (2006.01) | |
| C12P 19/34 | (2006.01) | |
| C07H 21/02 | (2006.01) | |
| C07H 21/04 | (2006.01) | |

(52) U.S. Cl.
CPC ........ *C12Q 1/6886* (2013.01); *C12Q 2523/125* (2013.01); *C12Q 2600/156* (2013.01); *C12Q 2600/136* (2013.01); *C12Q 2600/154* (2013.01)

(58) Field of Classification Search
CPC ........... C12Q 2600/154; C12Q 1/6886; C12Q 1/6881; C12Q 2600/118; C12Q 1/6883; C12Q 2600/156; C12Q 1/68; C12Q 1/686; C12Q 1/6876; C12Q 2523/125; C12Q 2600/136; A61L 2202/122; A61L 2202/22
See application file for complete search history.

(56) References Cited

U.S. PATENT DOCUMENTS

2007/0269823 A1* 11/2007 Huehn et al. ...................... 435/6

FOREIGN PATENT DOCUMENTS

| EP | 1 826 278 | 8/2007 |
| EP | 1 826 279 | 8/2007 |

OTHER PUBLICATIONS

Baron et al., "DNA demethylation in the human FOXP3 locus discriminates regulatory T cells from activated FOXP3+conventional T cells", *European Journal of Immunology*, 2007, vol. 37, No. 9, pp. 2378-2389.
Floess et al., "Epigenetic control of the *foxp3* locus in regulatory T cells", *PLoS Biology*, Feb. 2007, vol. 5, Issue 2, pp. 169-178.

* cited by examiner

*Primary Examiner* — Stephen Kapushoc
(74) *Attorney, Agent, or Firm* — Saliwanchik, Lloyd & Eisenschenk

(57) ABSTRACT

The present invention relates to a method, in particular an in vitro method for identifying FoxP3-positive CD25+CD4+ regulatory T cells of a mammal, comprising analyzing the methylation status of at least one CpG position in the FOXP3 gene, in particular its "upstream" regulatory regions, and in particular the promoter and the TSDR region of the gene foxp3, wherein a demethylation to at least 90% of at least one CpG in the sample as analyzed is indicative for a FoxP3-positive $CD25^+CD4^+$ regulatory T cell, and the use of said DNA-methylation analysis of the gene of the transcription factor FoxP3 for a detection and quality assurance and control of regulatory T cells. Furthermore, the present invention relates to a kit for performing the above methods as well as respective uses. The present invention furthermore provides an improved method for analyzing the methylation status of at least one CpG position in the gene foxp3 that allows for a precise analysis even from sub-optimal quality samples, such as non-freshly obtained blood or serum samples.

12 Claims, 7 Drawing Sheets

Figure 7

AMP5
5'-TGTCTGGGGGTAGAGGACCTAGAGGGCTGGGCAGCCGGCTGGGACGTCCCTTTCTGACTGGGTTCTC
AGAAGCTGAATGGGGGATGTTTCTGGACACAGATTATGTTTCATATCGGGGTCTCGCATCCGGCCCTGTTGTCACAGCCCCGACTT
GCCCAGATTTTCCGCCATTGACGTCATGCGCCGGATGCGCCGGCTTCATCGACACCACGGAGGAAGAGAAGAGGGCAGATACCCC
ACCCCACAGGTTTCGTTCCGAGAACTGGCTGCCCCTGTCCTGCAGCAGGCTTGGCCCAGTGGGGTGACA-3' (SEQ ID NO:1)

FoxP3MSP_For1 meth     GTTTTTCGATTTGTTTAGATTTTTTCGTT (SEQ ID NO:14)

non-meth GTTTTtGATTTGTTTAGATTTTTTtGTT (SEQ ID NO:15)

FoxP3MSP_Rev1 meth rev   CCTCTTCTCTTCCTCCTCCGTAATATACG (SEQ ID NO:16)

nm reverse CCTCTTCTCTTCCTCCTCCATAATATA (SEQ ID NO:17)

Probe non-methylated    776_209-222_nm ATGGTGGTTGGATGTGTTGGGTT (SEQ ID NO:18)
Probe methylated        776_209-222_m  ATGGGCGGTCGGATGCGTC (SEQ ID NO:19)

SEQUENCE LISTING

```
<160> NUMBER OF SEQ ID NOS: 19

<210> SEQ ID NO 1
<211> LENGTH: 336
<212> TYPE: DNA
<213> ORGANISM: Homo sapiens

<400> SEQUENCE: 1
tgtctggggg tagaggacct agagggccgg gctgggcagc cggcttcctg cactgtctgt      60
tgggacgtcc ctttctgact gggtttctca gaagctgaat gggggatgtt tctgggacac     120
agattatgtt ttcatatcgg ggtctgcatc tgggccctgt tgtcacagcc cccgacttgc     180
ccagattttt ccgccattga cgtcatggcg gccggatgcg ccgggcttca tcgacaccac     240
ggaggaagag aagagggcag ataccccacc ccacaggttt cgttccgaga actggctgcc     300
ctgtcctgca gcaggcttgg cccaggtggg gtgaca                              336

<210> SEQ ID NO 2
<211> LENGTH: 22
<212> TYPE: DNA
<213> ORGANISM: Homo sapiens
```

```
<400> SEQUENCE: 2
aaccctcaaa cctaactcat ac                                               22

<210> SEQ ID NO 3
<211> LENGTH: 22
<212> TYPE: DNA
<213> ORGANISM: Homo sapiens

<400> SEQUENCE: 3
ggaggtgata gtaaagaaag ga                                               22

<210> SEQ ID NO 4
<211> LENGTH: 20
<212> TYPE: DNA
<213> ORGANISM: Homo sapiens

<400> SEQUENCE: 4
tgtttggggg tagaggattt                                                  20

<210> SEQ ID NO 5
<211> LENGTH: 20
<212> TYPE: DNA
<213> ORGANISM: Homo sapiens

<400> SEQUENCE: 5
tatcacccca cctaaaccaa                                                  20

<210> SEQ ID NO 6
<211> LENGTH: 22
<212> TYPE: DNA
<213> ORGANISM: Homo sapiens

<400> SEQUENCE: 6
aaatcctaaa atctcaaaac ca                                               22

<210> SEQ ID NO 7
<211> LENGTH: 21
<212> TYPE: DNA
<213> ORGANISM: Homo sapiens

<400> SEQUENCE: 7
ggtgatgatg gaggtatgtt a                                                21

<210> SEQ ID NO 8
<211> LENGTH: 21
<212> TYPE: DNA
<213> ORGANISM: Homo sapiens

<400> SEQUENCE: 8
tagagatggt aataggggga g                                                21

<210> SEQ ID NO 9
<211> LENGTH: 22
<212> TYPE: DNA
<213> ORGANISM: Homo sapiens

<400> SEQUENCE: 9
ccaacctcac aaaaactaaa ct                                               22

<210> SEQ ID NO 10
<211> LENGTH: 22
<212> TYPE: DNA
```

<213> ORGANISM: Homo sapiens

<400> SEQUENCE: 10
gtgaggttgg gttttatatt gt                                    22

<210> SEQ ID NO 11
<211> LENGTH: 22
<212> TYPE: DNA
<213> ORGANISM: Homo sapiens

<400> SEQUENCE: 11
tatccctatc tctcaaccaa tc                                    22

<210> SEQ ID NO 12
<211> LENGTH: 20
<212> TYPE: DNA
<213> ORGANISM: Homo sapiens

<400> SEQUENCE: 12
tgtttggggg tagaggattt                                       20

<210> SEQ ID NO 13
<211> LENGTH: 20
<212> TYPE: DNA
<213> ORGANISM: Homo sapiens

<400> SEQUENCE: 13
tatcacccca cctaaaccaa                                       20

<210> SEQ ID NO 14
<211> LENGTH: 28
<212> TYPE: DNA
<213> ORGANISM: Homo sapiens

<400> SEQUENCE: 14
gttttcgatt tgtttagatt ttttcgtt                              28

<210> SEQ ID NO 15
<211> LENGTH: 28
<212> TYPE: DNA
<213> ORGANISM: Homo sapiens

<400> SEQUENCE: 15
gtttttgatt tgtttagatt tttttgtt                              28

<210> SEQ ID NO 16
<211> LENGTH: 25
<212> TYPE: DNA
<213> ORGANISM: Homo sapiens

<400> SEQUENCE: 16
cctcttctct tcctccgtaa tatcg                                 25

<210> SEQ ID NO 17
<211> LENGTH: 25
<212> TYPE: DNA
<213> ORGANISM: Homo sapiens

<400> SEQUENCE: 17
cctcttctct tcctccataa tatca                                 25

<210> SEQ ID NO 18
<211> LENGTH: 23

```
<212> TYPE: DNA
<213> ORGANISM: Homo sapiens

<400> SEQUENCE: 18
atggtggttg gatgtgttgg gtt                                              23

<210> SEQ ID NO 19
<211> LENGTH: 18
<212> TYPE: DNA
<213> ORGANISM: Homo sapiens

<400> SEQUENCE: 19
atggcggtcg gatgcgtc                                                    18
```

DNA METHYLATION ANALYSIS OF REGULATORY T CELLS THROUGH DNA-METHYLATION ANALYSIS OF THE TSDR REGION OF THE GENE FOXP3

CROSS REFERENCE TO A RELATED APPLICATION

This application is a National Stage Application of International Application Number PCT/EP2009/004793, filed Jul. 2, 2009; which claims priority to European Application No. 08012056.1, filed Jul. 3, 2008; both of which are incorporated herein by reference in their entirety.

The present invention relates to a method, in particular an in vitro method for identifying FoxP3-positive $CD25^+CD4^+$ regulatory T cells of a mammal, comprising analyzing the methylation status of at least one CpG position in the FOXP3 gene, in particular its "upstream" regulatory regions, and in particular the promoter and the TSDR region of the gene foxp3, wherein a demethylation to at least 90% of at least one CpG in the sample as analyzed is indicative for a FoxP3-positive $CD25^+CD4^+$ regulatory T cell, and the use of said DNA-methylation analysis of the gene of the transcription factor FoxP3 for a detection and quality assurance and control of regulatory T cells. Furthermore, the present invention relates to a kit for performing the above methods as well as respective uses. The present invention furthermore provides an improved method for analyzing the methylation status of at least one CpG position in the gene foxp3 that allows for a precise analysis even from sub-optimal quality samples, such as non-freshly obtained blood or serum samples.

BACKGROUND OF THE INVENTION

Regulatory T cells (Treg or Tregs) have become a major focus of immunological research due to their role as interface between establishing tolerance against harmless self and foreign antigens on one side and allowing counteraction against harmful antigens on the other side. Increased levels of Treg have been found in many human cancers. This has promoted the theory that dysregulation of Treg levels leads to overzealous tolerance against tumor cells. The Treg property to dampen immune reactions is also important for therapeutic strategies involving modulation of the immune system.

The transcription factor Foxp3 is specifically expressed in regulatory T cells and is thought to function as a master switch for the development and function of these cells. Recently, it has been demonstrated that ectopic expression of Foxp3 in conventional T cells confers suppressive activity (Fontenot and Rudensky, Nat Immunol 6:331-337, 2005).

The vast majority of Foxp3+ regulatory T cells is generated during T cell development within the thymus, and it is thought that they represent an individual lineage. In addition, it also has been reported that Foxp3+ regulatory T cells arise from conventional T cells both in vitro and in vivo upon antigen recognition under tolerogenic conditions. In all cases the expression of Foxp3 is characteristic for the development of regulatory T cells.

It is largely unknown, which signals lead to the expression of Foxp3, although some factors including TGF-β have been reported to induce Foxp3 expression in conventional T cells. However, it is unknown if TGF-β induction leads to a full differentiation into a Treg, or merely to an only transiently FOXP3 expressing T cells, with or without a suppressive phenotype. Therefore, the starting point for the present invention was the search for phenotypes clearly related to T cells having a stable suppressive phenotype.

One obstacle for monitoring Treg levels is that the best current detection method, the analysis of FOXP3 and CD25 mRNA and/or protein, detects both, Tregs and activated T-cells, and is therefore unable to distinguish between these phenotypes.

Even though almost all cells in an individual contain the exact same complement of DNA code, higher organisms must impose and maintain different patterns of gene expression in the various tissue types. Most gene regulation is transitory, depending on the current state of the cell and changes in external stimuli. Persistent regulation, on the other hand, is a primary role of epigenetics—heritable regulatory patterns that do not alter the basic genetic coding of the DNA. DNA methylation is the archetypical form of epigenetic regulation; it serves as the stable memory for cells and performs a crucial role in maintaining the long-term identity of various cell types.

The primary target of methylation is the two-nucleotide sequence Cytosine-Guanine (a 'CpG site'); within this context cytosine (C) can undergo a simple chemical modification to become 5-methyl-cytosine. In the human genome, the CG sequence is much rarer than expected except in certain relatively dense clusters called 'CpG islands'. CpG islands are frequently associated with gene promoters, and it has been estimated that more than half of the human genes have CpG islands (Antequera and Bird, Proc Natl Acad Sci USA. 90:11995-9, 1993).

Aberrant methylation of DNA frequently accompanies the transformation from healthy to cancerous cells. Among the observed effects are genome-wide hypomethylation, increased methylation of tumor suppressor genes and hypomethylation of many oncogenes (reviewed by Jones and Laird, Nature Genetics 21:163-167, 1999; Esteller, Oncogene 21:5427-5440, 2002; Laird, Nature Reviews/Cancer 3:253-266, 2003). Methylation profiles have been recognized to be tumor specific (i.e., changes in the methylation pattern of particular genes or even individual CpGs are diagnostic of particular tumor types) and there is now an extensive collection of diagnostic markers for bladder, breast, colon, esophagus, stomach, liver, lung, and prostate cancers (summarized by Laird, Nature Reviews/Cancer 3:253-266, 2003).

Chen et al. (Chen L, Cohen A C, Lewis D B. Impaired Allogeneic Activation and T-helper 1 Differentiation of Human Cord Blood Naive CD4 T Cells. Biol Blood Marrow Transplant. 2006 February; 12(2):160-71) describe FoxP3 protein expression as a marker for regulatory CD25(high) CD4 T cells.

EP 1213360 describes a method of identifying a cell, tissue or nucleus, comprising collecting information on the methylation pattern of DNA isolated from the cell, tissue or nucleus and analyzing the resultant information.

WO 2004/050706 describes a sub-group of T-cells, and relates to characteristics of regulatory T-cells which define them as such. The application also describes the uses of such T-cells, compositions comprising them and chemokines which recruit them in the modulation of an immune response.

Finally, EP 1826279 describes a method, in particular an in vitro method for identifying FoxP3-positive regulatory T cells, preferably $CD25^+$ $CD4^+$ regulatory T cells of a mammal, comprising analyzing the methylation status of at least one CpG position in the gene foxp3 or an orthologous or paralogous gene thereof, and the use of DNA-methylation analysis of the gene of the transcription factor FoxP3 for a detection and quality assurance and control of regulatory T cells.

In view of the above, it is an object of the present invention, to provide an improved method based on DNA methylation analysis as a superior tool in order to more conveniently and reliably identify FoxP3-positive stable regulatory T cells, preferably CD25+CD4+ regulatory T cells, derived from a mammal, and/or in a mammal. Furthermore, reliable detection of the phenotype should be available independently of purity, storage, and to some extent also of tissue quality.

SUMMARY OF THE INVENTION

According to a first aspect thereof, the present invention solves the above objects by providing a method for identifying FoxP3-positive CD25+CD4+ regulatory T cells of a mammal, comprising analyzing the methylation status of at least one CpG position in one or more regulatory regions of the foxp3 gene, in particular (and preferably) in the TSDR region of the gene foxp3, wherein a demethylation of at least one CpG to at least 90% is indicative for a FoxP3-positive CD25+ CD4+ regulatory T cell. The term "a demethylation of at least one CpG to at least 90%" shall mean that the 90% refer to the methylation level of one individual CpG (as analyzed) in a cell in one allele. Said CpG position can be located in a regulatory region, such as the region upstream of the transcription start site, such as in the CpG island region(s), the promoter region, or the TSDR region of the gene foxp3, for example according to SEQ ID No. 1, or any other sequence contained in the foxp3 locus, wherein a demethylation (preferably of at least one CpG to at least 90%) is indicative for a FoxP3-positive CD25+CD4+ regulatory T cell.

In another preferred embodiment of the present invention, the inventors furthermore present a novel and more specific way to monitor Treg levels in mammalian, e.g. and in particular human samples, such as whole blood fractions of blood, fresh or frozen tissue, paraffin-embedded tissue, and/or cultures, and in other body fluids, any given (solid) tissue, organ or cell type that is suspected of containing Tregs.

The inventive assay is based on specific demethylation of the FOXP3 promoter found in Tregs (TSDR, Treg specific demethylated region). Using a simple and precise quantitative PCR method, the inventors show that FOXP3 demethylation represents a surrogate marker for Treg counts, avoiding co-measurement of activated FOXP3+ T cells. The precision and quality of this assay was shown in various studies. As far as blood is concerned, the method was verified in an IL2 immunotherapy set-up, in purified blood cell subtypes, in solid tumors, and healthy solid tissue. The present inventors have thus identified particular regions within the Foxp3 gene that are functionally involved in, or mandatorily associated with the existence of stable, potentially FOXP3 positive, (mostly) functionally suppressive regulatory T cells. In one preferred embodiment, one particularly suitable region is either the promoter or the TSDR exhibiting for example the nucleotide sequence according to SEQ ID No. 1.

The inventors could further demonstrate that in Foxp3+ cells the CpGs in the motifs as above are almost completely demethylated (i.e. to more than 70%, preferably 80%, preferably, more than 90%, and most preferred more than 95%), whereas the same motifs are completely methylated in Foxp3− cells. The differential methylation of the CpG motifs within the aforementioned regions seems to correlate with Foxp3 expression, although the correlation is best between the Treg phenotype (the actual suppressor phenotype) and FoxP3 demethylation in that it indicates stable, long term expression of FoxP3 (and thus stable Tregs), and not with transient expression which leads to only transient or no suppression). Thus, determination of the methylation status of the Foxp3 locus is a valuable tool to identify stable populations of regulatory T cells, such as will be required/or at least of some value for measuring Treg in the diagnosis of autoimmune diseases, transplant rejections, cancer allergy, or the Treg related immune status in any envisionable context, as desired. The assay according to the present invention allows for measurements to identify a Treg without purification or any staining procedures. It even works in solid tumors or other solid tissues.

The present invention relies on the surprising finding that in a particular region of the gene for FoxP3, the so-called "TSDR" (Treg specific demethylated region), the CpG motifs are almost completely demethylated (i.e. to more than 90%, preferably 91%, preferably, more than 92% and most preferred more than 95%), whereas the same motifs are completely methylated in all non Treg (Foxp3− cells). Thus, this region provides a valuable and reliable tool for a diagnostic analysis according to the present invention. Surprisingly, the methylation is not necessarily 1:1 related with gene expression but much rather with the actual cell type function, i.e., the suppressive phenotype.

The inventors have previously shown both in man and mice that constitutive expression of FoxP3 in naturally occurring Treg always coincides with epigenetic, i.e., DNA methylation based regulation. DNA methylation is a biologically and chemically stable epigenetic modification, resulting in longterm gene expression changes. Demethylation at the human FOXP3 locus was found to be restricted to Treg when tested against all major peripheral blood cell types and a selection of non-blood cells. Beside the high specificity for Treg, it was also observed that FoxP3 demethylation occurred only in natural Treg, but not in activated conventional T cells transiently expressing FoxP3. It was further associated with stable FOXP3 expression upon Treg in vitro expansion. These data indicated that epigenetic modifications in the FoxP3 locus serve as valuable marker for the identification of cells with stable Treg phenotype and not activated T-cells.

In a preferred embodiment of the method according to the present invention, said analysis of the methylation status comprises amplification with at least one primer of the primer pairs selected from SEQ ID No. SEQ ID No 2 to 17 and in particular SEQ ID No. SEQ ID No. 4 and 5.

Preferably, the amplification involves a polymerase enzyme, a PCR or chemical amplification reaction, or other amplification methods as known to the person of skill as described below, e.g. in the context of MSP, HeavyMethyl, Scorpion, MS-SNUPE, MethyLight, sequencing, methyl specific restriction assays, and the like, and combinations thereof such as MSP coupled with probe based detection, wherein the probe may be methylation-specific (Methylight) or methylation unspecific. With the amplification, the amplicon of the TSDR or any other region in the FoxP3 gene or any paralog or ortholog as described herein is produced that is a particularly preferred "tool" for performing the method(s) according to the present invention. Consequently, an oligomer according to any of SEQ ID No. 2 to 11 or the amplicon as amplified by the primer pair selected from SEQ ID No. 4 and 5 constitute preferred embodiments of the present invention, together with a probe according to SEQ ID Nos 18 to 19 or other suitable sequences in the FOXP3 locus.

The person of skill will furthermore be able to select specific subsets of CpG positions in order to minimize the amount of sites to be analyzed, for example all sites as present on the amplicon according to SEQ ID No 1 or other suitable sequences in the FoxP3 locus, such as the promoter sequences.

In order to analyze the methylation status of a CpG position or positions, any known method to analyze DNA methylation can be used. In a preferred embodiment of the method according to the present invention, the analysis of the methylation status comprises a method selected from methylation specific enzymatic digests, bisulphite sequencing, analysis selected from promoter methylation, CpG island methylation, MSP, HeavyMethyl, MethyLight, Ms-SNuPE or other methods relying on a detection of amplified DNA. These methods are well known to the person of skill, and can be found in the respective literature.

The method according to the present invention can be performed with any mammal having the foxp3 gene or an ortholog or paralog thereof, preferred is a method according to the present invention, wherein said mammal is a mouse, rat, rodent, dog, cat, pig, monkey or human.

In another aspect of the present invention, the method according to the present invention further comprises an induction with TGF-β, other cytokines or cytokine-like proteins, functional cytokine equivalents or the like. A critical issue for application of regulatory T cells and other leukocytes in therapeutic approaches is the availability of large numbers of cells or the generation of various sorts of leukocyte cell types which can be induced in vitro or in vivo by cytokine challenge. Recent publications have reported that conventional CD25$^-$ CD4$^+$ T cells can be converted into Foxp3$^+$ regulatory T cells by stimulation in presence of TGF-β (Chen W, Jin W, Hardegen N, Lei K J, Li L, Marinos N, McGrady G, Wahl S M. Conversion of peripheral CD4$^+$CD25$^-$ naive T cells to CD4$^+$CD25$^+$ regulatory T cells by TGF-beta induction of transcription factor Foxp3. J Exp Med. 2003 Dec. 15; 198(12):1875-86.), (Park H B, Paik D J, Jong E, Hong S, Youn J. Acquisition of anergic and suppressive activities in transforming growth factor-beta-costimulated CD4$^+$CD25$^-$ T cells. Int Immunol. 2004 August; 16(8):1203-13. Epub 2004 Jul. 5), (Fu S, Zhang N, Yopp A C, Chen D, Mao M, Chen D, Zhang H, Ding Y, Bromberg J S. TGF-beta induces Foxp3+ T-regulatory cells from CD4+CD25-precursors. Am J. Transplant. 2004 October; 4(10):1614-27), (Fantini M C, Becker C, Monteleone G, Pallone F, Galle P R, Neurath M F. Cutting edge: TGF-beta induces a regulatory phenotype in CD4+CD25− T cells through Foxp3 induction and down-regulation of Smad7. J. Immunol. 2004 May 1; 172(9):5149-53), (Wan Y Y, Flavell R A. Identifying Foxp3-expressing suppressor T cells with a bicistronic reporter. Proc Natl Acad Sci USA. 2005 Apr. 5; 102(14):5126-31. Epub 2005 Mar. 28), (Fantini M C, Becker C, Tubbe I, Nikolaev A, Lehr H A, Galle P R, Neurath M F. TGF-(beta) induced Foxp3+ regulatory T cells suppress Th1-mediated experimental colitis. Gut. 2005 Sep. 14). However, stability and in vivo efficacy of these cells have not been thoroughly tested so far. Analysis of the accessibility of the Foxp3 locus is a better marker for the existence of Treg or other functionally equivalent cells than the mere expression of Foxp3, to what extent a permanent conversion into a regulatory T cell lineage did occur or to determine the in vivo status/activity. The inventors therefore analyzed the methylation status of the Foxp3 locus from CD25$^-$CD4$^+$ T cells, which had been activated and cultured for 5 days in the presence of TGF-β or other cytokines or cytokine-like proteins, functional cytokine equivalents or the like. On day 5, control cells cultured under Th1 conditions showed minor Foxp3-expression (<2%), whereas almost 95% of the cells stimulated in the presence of TGF-β were Foxp3$^+$ with partial demethylation (FIG. 2A). Interestingly, a partial demethylation was only observed in the cells stimulated in the presence of TGF-β.

In another aspect of the present invention, the present invention provides a method for diagnosing the immune status of a mammal, comprising the steps of a) obtaining a sample containing T-cells from said mammal to be diagnosed, b) analyzing the methylation status of at least one CpG position in the gene foxp3 or an orthologous or paralogous gene thereof according to the present invention in said T-cells, c) identifying the amount of regulatory T-cells present in said sample based on said methylation status, and d) concluding on the immune status of said mammal based on said amount as identified. In one aspect of this particular method, the total population of cells in a sample (of e.g. whole blood, any other full tissue, pre-sorted or sorted subtractions of any tissues, (e.g. blood such as buffy coat), organs or cells that contain at least one of the two cell types: regulatory T-cells and non-regulatory cells) is analyzed for their methylation status in the foxp3 gene. Based on the result of the overall methylation frequency of the sites, the ratio and/or amount of regulatory T cells inside the analyzed population can be determined. From said result, it can be concluded on the immune status and/or T cell status of the mammal as diagnosed. The method can be performed in vitro and/or in vivo. In general, all biological samples can be used, as long as they contain suitable T-cells. Preferred is a method, wherein said sample is selected from a blood sample, a buffy coat sample, a sample of blood lymphocytes or a fraction thereof, or biopsy samples or body fluids.

The method according to the present invention can be performed with any mammal having the foxp3 gene or an ortholog or paralog thereof, preferred is a method according to the present invention, wherein said mammal is a mouse, rat, monkey or human. Preferred is a method, wherein said mammal is a patient suffering from a disease selected from autoimmune diseases, adverse effects in allotransplant recipients, tumorous diseases, ovarian cancer, chronic graft-versus-host disease, allergic asthma, Lepra, and multiple sclerosis.

Further preferred is a method, wherein the amount of regulatory T-cells corresponds to a demethylation of the CpG positions as analyzed to at least 90%, preferably 91%, and more preferably 92%.

Even further preferred is a method that further comprises measuring and/or monitoring the amount or ratio of said regulatory T cells in response to chemical and/or biological substances that preferably modulate foxp3 expression in the regulatory T cell. That is, changes in the amount or ratio of regulatory T cells that are caused by, for example, the treatment of a disease (e.g. as described herein), and the success and/or progress of said treatment in terms of an effect on regulatory T cells can be followed using this method. A follow-up of the methylation pattern of the FoxP3 marker in the measured sample will indicate changes in the cells that are due to a response to said chemical and/or biological substances, in some cases even before a phenotypic change can be observed.

In yet another aspect of the present invention, the present invention provides a method for determining the suitability of in vitro generated or expanded regulatory T cells or other cellular transplants that may contain Tregs either as an desired component or as a putative contaminant (i.e. adversary to the medical intention) for a transfer into a patient, comprising the method according to the present invention, and detecting, whether the CpG positions as analyzed are demethylated to at least 90%, preferably 91%, and more preferably 92%. The method can be performed in vitro and/or in vivo. For example, T cells that appear to show a modified, in particular a drop, of foxp3 CpG methylation are usually not regarded as stable and will not be used further.

In yet another aspect of the present invention, the present invention provides a method for identifying chemical and/or biological substances that modulate foxp3 methylation in a T cell comprising contacting one or more of said chemical and/or biological substance with a T cell, performing the method according to the present invention as described above, and detecting, whether said chemical and/or biological substance modulates methylation of the CpG positions as analyzed. The method can be performed in vitro and/or in vivo. In this aspect, the present invention encompasses a method, sometimes called a "screening-method", that seeks to identify chemical and/or biological substances modulating foxp3 demethylation that is indicative for the long-term phenotype of a suppressor T cell type (herein also named "Treg epigenotype"). These substances as identified can be used as starting points for the development of regulatory T cell specific medication and respective pharmaceutical compositions.

The assay of the present invention is based on the alternative method of detecting Tregs by not (or not directly) detecting gene expression of the marker FoxP3, but rather detecting the general characteristic of the short-term or long-term, or stabilizing activation of the gene of FoxP3 through methylation analysis. This stands in contrast to measuring expression, which shows an "analogue" mode of change (from no to a bit, to a bit more to lots and . . . ) and is also expressed to a certain extend "before" and without a definitive commitment towards Treg.

The present method is further based on the fact that it is well accepted that the foxp3 gene plays a central role for the development of regulatory T cells. Therefore, factors modulating Foxp3 expression are also interesting tools to treat autoimmune diseases or allotransplantate recipients.

Foxp3$^+$ regulatory T cells have been shown to prevent a strong anti tumor response, therefore factors that inhibit the production/activity of Treg are also interesting for the treatment of tumor patients. Such factors, which lead to a stable modification of Foxp3 methylation—and thus stable Tregs—can be detected with the method described in this invention.

Furthermore, factors that can enhance the differentiation of regulatory T-cells and lead to an alleviation of autoimmune and allergenic disorders can be identified with the present method. Chemical and/or biological substances that are suitable as screening compounds are known to the person of skill and, for example, include small molecules, peptides and proteins, and anti-bodies or fragments thereof. Furthermore, the screening can be done using a commercially compound library, optimally together with suitable automation, such as a robot. In one preferred embodiment of the method for identifying chemical and/or biological substances, said substance provides a demethylation of the CpG positions as analyzed to at least 90%, preferably 91%, and more preferably 92%.

The expression of FoxP3 is described as being associated with poor prognosis in ovarian cancer (Wolf, D., et al. The expression of the regulatory T cell-specific forkhead box transcription factor FoxP3 is associated with poor prognosis in ovarian cancer. Clin. Cancer Res. 11 (23), 8326-8331 (2005)). High expression levels of FoxP3 are associated with ovarian cancer. Furthermore, the gene expression of regulatory T cells transcription factor FOXP3 was reduced in chronic graft-versus-host disease patients (Zorn, E., et al. Reduced frequency of FOXP3+CD4+CD25+ regulatory T cells in patients with chronic graft-versus-host disease. Blood 106 (8), 2903-2911 (2005)) In addition, a role of FoxP3 in allergic asthma has been described (Schmidt-Weber, C. B. and Blaser, K. The role of the FOXP3 transcription factor in the immune regulation of allergic asthma. Curr Allergy Asthma Rep 5 (5), 356-361 (2005)).

Thus, another preferred method according to the present invention is a method for the diagnosis of diseases that are associated with the aberrant (or undesired) number of Tregs, comprising the method according to the present invention, and detecting, whether the CpG positions as analyzed are demethylated to at least 90%, preferably 91%, and more preferably 92%, wherein the diseases are selected from autoimmune diseases, adverse effects in allotransplantate recipients, tumorous diseases, ovarian cancer, chronic graft-versus-host disease, allergic asthma. The present method can be performed in vitro and/or in vivo, and allows for a more specific determination of the parameter FoxP3, as temporary expression of FoxP3, especially in the human system, has been detected also in activated, non-regulatory T cells (Ziegler S F. FOXP3: Of Mice and Men. Annu Rev Immunol. 2005 Dec. 1).

Another preferred aspect of the present invention relates to a kit for identifying regulatory T cells based on the analysis of the methylation status of CpG positions in the gene foxp3, comprising materials for performing a method according to the present invention. In one preferred embodiment according to the present invention, the kit comprises a) a bisulfite reagent, and b) materials for the methylation analysis of CpG positions in the TSDR or other suitable regions in the FoxP3 gene, such as the promoter region. The person of skill will furthermore be able to select materials for specific subsets of CpG positions in order to minimize the amount of sites to be analyzed, for example all sites as present on the amplicon according to SEQ ID No. 1 (or the other suitable CpG containing regions in the gene. The kit can be a diagnostic kit.

The kits according to the present invention may also contain: 1. Chemicals (bisulfite, etc.) for processing the cell samples; 2. Procedure protocols; 3. Oligonucleotide probes, amplicons, template DNA in bisulfite treated or non-bisulfite treated versions, blockers and/or extension primers, and enzymes, tools (including columns, tubes etc.) according to the present invention that will detect markers relevant to a particular cell type. The oligonucleotides would be constructed to generate a signal on a commonly available detection platform, such as regular PCR, Real Time-PCR (RT-PCR) or Single Base Extension (SBE), sequencing. Each signal indicates the level of methylation at a particular target site in the sample. As an alternative, probes according to the described nucleic acids could be produced for usage on a chip; 4. A bioinformatic tool to process the results. This, e.g., software might normalize the signals from the raw data, contain a result matrix for interpretation of the read-out, or implement various algorithms that calculate, for example, cell type proportions, or potency predictions.

Yet another preferred aspect of the present invention relates to the use of an oligomer, a probe or amplicon or template DNA according to the present invention or a kit according to the present invention for detecting and/or identifying FoxP3-positive regulatory T cells, preferably CD25$^+$CD4$^+$ regulatory T cells, in analogy to what has been described above.

Yet another preferred aspect of the present invention relates to a method of treatment of diseases that are related to Foxp3 expression, such as autoimmune diseases, adverse effects in allotransplantate recipients, tumorous diseases, ovarian cancer, chronic graft-versus-host disease, allergic asthma, multiple sclerosis. The method comprises administering an effective amount of stable FoxP3-positive regulatory T cells, preferably CD25$^+$CD4$^+$ regulatory T cells to said patient in need thereof. How to administer effective amount of stable FoxP3-positive regulatory T cells, preferably stable CD25$^+$CD4$^+$ regulatory T cells is described in the literature (for example in Bharat A, Fields R C, Mohanakumar T. Regulatory T cell-mediated trans-plantation tolerance. Immunol Res. 2006; 33(3):195-212. June C H, Blazar B R. Clinical application of expanded CD4(+)25(+) cells. Semin Immunol. 2006 Jan. 31; Khazaie K, von Boehmer H. The impact of CD4(+)CD25(+) Treg on tumor specific CD8(+) T cell cytotoxicity and cancer. Semin Cancer Biol. 2006 April; 16(2): 124-136. Epub 2006 Jan. 26, and the references as cited therein), and the person of skill will be able to apply these methods in the context of the present invention. The term "treatment" also includes a prevention of said Foxp3 expression related diseases.

Yet another preferred aspect of the present invention relates to a method of treatment of a disease, comprising the method according to the present invention as above, and administering Tregs when said method detects low counts of Tregs in said patient, or administering a Treg-count-lowering drug or when said method detects elevated counts of Tregs in said patient. Preferred examples of the diseases to be treated are autoimmune diseases, when low counts of Tregs are detected in said patient, and tumorous diseases where higher than normal counts of Tregs are detected in said patient. Preferably, the method according to the invention can be used as so-called "companion diagnostics" for an administration of a Treg-count-lowering medication, e.g. as a direct drug (such as low dose cyclophosohamide, thalodomide, Ontak and others) or as an inductor for improved cancer vaccination strategies, for example, by peptide based vaccines, humanized or mouse antibodies, and/or anti-idiotype monoclonal antibodies, or the like.

Yet another preferred aspect of the present invention relates to a method for prognosing and/or predicting the outcome of cancer, comprising a method according to the present invention, and prognosing and/or predicting the outcome of said cancer based on a Treg count as detected, wherein an increased number of tumor infiltrating Treg in the sample as analyzed is prognostic and/or predictive for the outcome of said cancer. Preferably, said sample is tumor tissue, and said disease is ovarian cancer.

Yet another preferred aspect of the present invention relates to a method for the analysis of the methylation status of the TSDR region or any other suitable region within the foxp3 locus in order to allow a prediction, whether the cell population stably expresses the FoxP3 gene, or not. Therefore, this method can be used as a quality control for in vitro generated and/or expanded regulatory T cells before adoptive transfer into patients which suffer from autoimmune diseases or which have received an allotransplant. Only if the CpG motifs are demethylated to a certain degree (such as to more than 90%, preferably 95%, and more preferably 98%), one can be confident that these cells will stably express the Foxp3 gene and will not loose foxp3 expression after some period of time. The latter scenario is contraindicative, since the adoptively transferred cells could convert from Foxp3$^+$ regulatory T cells into effector cells, which might lead to a worsening of the disease state. Therefore, in such a setting a quality control concerning the stability of the regulatory phenotype of adoptively transferred cells is absolutely mandatory, and can be readily achieved by the analysis of the methylation status of the aforementioned region(s) of the Foxp3 locus.

In another aspect of the present invention, the present invention provides a method for diagnosing cutaneous T cell lymphoma (CTCL) in a mammal, comprising the steps of performing a method according to the present invention, and detecting the amount of CD25$^{++}$ cells based on the methylation state of the gene for FoxP3. Yet another preferred aspect of the present invention relates to a method of treatment of CTCL, comprising a) treating the mammal with a suitable medicament against CTCL, such as ONTAK, b) performing the method according to the present invention as above, and prognosing and/or predicting the efficacy of said medicament in treating said CTCL based on the amount of CD25$^{++}$ cells as identified based on the methylation state of the gene for FoxP3. In one embodiment of said method, the attending physician will decide about the further treatment of the CTCL (for example the further use or the discontinuation of ONTAK), at least in part, based on the results as obtained using said method of the invention.

Yet another preferred aspect of the present invention relates to a method of treatment of malignant melanoma, comprising detecting the amount, presence and/or number of Tregs in a sample derived from a sentinel lymph node based on the methylation state of the gene for FoxP3 according to the present invention, and continuing/discontinuing a treatment of said malignant melanoma based on the amount, presence and/or number of Tregs as identified, wherein a change in the amount, presence and/or number of Tregs is indicative for a higher potential for a relapse.

In summary, the present invention relate to a method for identifying FoxP3-positive CD25$^+$CD4$^+$ regulatory T cells of a mammal, comprising analyzing the methylation status of at least one CpG position in one or more regulatory regions of the foxp3 gene, such as in the TSDR region, wherein a demethylation of said at least one CpG to at least 90% is indicative for a FoxP3-positive CD25$^+$CD4$^+$ regulatory T cell. Preferably, said CpG position is located in a regulatory region selected from the upstream region, such as in the CpG island, the promoter region, and/or the TSDR region of the gene foxp3.

Further preferred is a method according to the present invention, wherein a demethylation of at least one CpG in one allele, in one cell to at least 91%, preferably at least 92% or more is indicative for a FoxP3-positive CD25$^+$CD4$^+$ regulatory T cell.

Preferably, said regulatory T cells are stable regulatory T cells.

Advantageously, the method according to the present invention can be performed in a sample selected from the group of whole blood, paraffin-embedded tissue, fractions of blood, tissue, solid tissue, cell or tissue cultures, body fluids, organs and other samples that are suspected of containing Tregs. Said analysis of the methylation status can comprise a method comprising methylation specific enzymatic digests, promoter methylation, CpG island methylation, bisulphite sequencing, MSP, HeavyMethyl, MethyLight, Ms-SNuPE, PCR and/or real time PCR.

Preferably, said analysis of the methylation status comprises amplification with at least one primer of the primer pairs selected from SEQ ID No. SEQ ID No. 4 and 5 and SEQ ID No. SEQ ID No. 6 and 7. Preferably, said analysis of the methylation status comprises analyzing the methylation status of at least one CpG position as analyzed by any of the probes according to SEQ ID Nos 17 to 18.

Further preferred is a method according to the present invention, wherein said mammal is a mouse, rat, rodent, dog, cat, pig, monkey or human. Further preferred is a method according to the present invention, further comprising an induction with TGF-β or other cytokine like factors.

Particularly preferred is a method according to the present invention, comprising the following steps: a) providing a conserved tissue sample of a mammalian origin, such as a paraffin embedded sample, b) analyzing the methylation status in at least one CpG position in the foxp3 gene of said sample, and c) identifying the amount of regulatory T-cells present in said sample based on said methylation status. A conserved tissue sample means a non-freshly taken sample of mammalian origin to be analyzed and said sample can selected from the group of whole blood, paraffin-embedded tissue, fractions of blood, tissue, solid tissue, cell or tissue cultures, body fluids, organs and other samples that are suspected of containing Tregs. Preferred are samples of paraffin-embedded tissue, fractions of blood, tissue, solid tissue, cell or tissue cultures. Preferably, said method further comprises concluding on the tissue status, with respect to Treg infiltration and FoxP3 expression status of said tissue.

Another aspect of the present invention then relates to a method for diagnosing the immune status of a mammal, comprising the steps of a) providing a sample containing T-cells from said mammal to be diagnosed, b) analyzing the methylation status of at least one CpG position in the foxp3 gene, c) identifying the amount of regulatory T-cells present in said sample based on said methylation status, and d) concluding on the immune status of said mammal based on said amount as identified. Preferably, as also stated above, said CpG position is located in the upstream region, such as in the CpG island, the promoter region, or the TSDR region of the gene foxp3. Preferably, a demethylation of at least one CpG of in one allel, in one cell to at least 91%, preferably at least 92% or more is indicative for a FoxP3-positive CD25$^+$CD4$^+$ regulatory T cell. Further preferred, said analysis of the methylation status is performed in a sample selected from the group of whole blood, paraffin-embedded tissue, fractions of blood, tissue, solid tissue, cell or tissue cultures, body fluids, organs and other samples that are suspected of containing Tregs. Further preferred, said method is performed in individuals as a preventive detection of tumorous diseases, Preferably, said mammal is a patient suffering from a disease selected from autoimmune diseases, adverse effects in allo-transplantate recipients, tumorous diseases, such as ovarian cancer, chronic graft-versus-host disease, allergic asthma, and multiple sclerosis.

Another aspect of the present invention the relates to a method according to the present invention, further comprising measuring and/or monitoring the amount of said regulatory T cells in response to chemical and/or biological substances that are suspected to modulate FoxP3 expression in the regulatory T cell, modify the amounts of Tregs, or to modulate Treg expansion, Treg levels, Treg migration behaviour, or Treg survival.

Another aspect of the present invention then relates to an in vitro method for determining the suitability and or quantity of in vitro generated or expanded regulatory T cells for a transfer into a patient, comprising the method according to the present invention, and detecting, whether the CpG positions as analyzed are demethylated to at least 90%, preferably 91%, and more preferably 92%.

Another aspect of the present invention then relates to an in vitro method for identifying chemical and/or biological substances and or culture conditions that modulate foxp3 expression in a T cell, stem cell or progenitor cell or Treg proliferation, differentiation survival and cell death, comprising contacting one or more of said chemical and/or biological substance with a T cell, performing the method according to the present invention, and detecting, whether said chemical and/or biological substance or conditions modulates methylation of the CpG positions as analyzed. Preferred is the method for identifying chemical and/or biological substances according to the present invention, wherein said substance provides an increase of demethylation of the CpG positions as analyzed to at least 90%, preferably 91%, and more preferably 92%.

Another aspect of the present invention then relates to an oligomer according to any of SEQ ID No. 2 to 17 or an amplified nucleic acid according to SEQ ID No. 1.

Another aspect of the present invention then relates to a method of treating a disease in a patient, comprising a method according to the present invention, and treating said disease of said patient based on the amount of CD25$^+$CD4$^+$ regulatory T cells as determined, and as described above. Preferably, said disease is selected from autoimmune diseases, adverse effects in allo-transplantate recipients, tumorous diseases, such as ovarian cancer, chronic graft-versus-host disease, allergic asthma, Lepra and multiple sclerosis. Preferably, said treatment is selected from chemotherapies, antibody-based treatments, biological drug testing, such as vaccine approaches, Treg killing substances, cytokines, cytostatics, and chemical compounds reducing the Treg counts, such as thalidomide.

Another aspect of the present invention then relates to a kit for identifying regulatory T cells based on the analysis of the methylation status of CpG positions in the gene foxp3, comprising materials for performing a method according to the present invention.

Another aspect of the present invention then relates to the use of an oligomer or amplified nucleic acid according to the present invention or a kit according to the present invention for detecting and/or identifying FoxP3-positive regulatory T cells, preferably CD25$^+$CD4$^+$ regulatory T cells.

The present invention shall now be further described in the following examples without being limited thereto. For the purpose of the present invention all references as cited herein as well as the sequence listing are incorporated by reference in their entireties. In the accompanying Figures and Sequences, FIG. 1 shows the quantitative PCR system for the FOXP3 TSDR. A) depicts the FOXP3 locus and the amplification strategy. Two methyl sensitive amplification primers and methyl sensitive hybridization probes were designed. The detection dye, which is quenched whilst the probe is intact, is released upon exonuclease digest during specific strand elongation. B) The plots in the upper two rows show amplification profiles of the qPCR systems. In the left panels, the non-methylation-specific, and in the right panels the methylation-specific amplification system is shown. In the upper row, a plasmid corresponding non-methylated DNA (all Cs in the TSDR replaced by T) is used in a dilution row from 200 million to 20 copies is used. The same dilution is shown in the middle panels with a plasmid corresponding the methylated DNA (all Cs other than in the context CG replaced by T). In the lower panel the standard curve as produced by the plasmid dilution system presents itself strictly log linear.

FIG. 2 shows the analysis of $T_{reg}$ and $T_{naïve}$ using FACS or qPCR. A) FACS analysis of PBMC from a male (upper panel) and a female donor (lower panel) separated into CD25$^{++}$ (left panel) and CD25$^-$ (right panel) cells. Cells were fixed, stained and FACS-counted with FOXP3 antibody. Numbers indicate the percentile level of FOXP3$^+$ cells. B) qPCR amplification plots for FACS sorted CD25$^{++}$ cells and CD25 cells, each for the male and female donor presented in A. Numbers represent the copy numbers for non-methylated (nm) DNA in the left and methylated DNA (m) in the right panel. The numbers in the table indicate the percentile number of Treg as determined FOXP3 protein expressing cells or FOXP3 demethylated cells in the methylated fraction.

FIG. 3 shows the Treg count in the PBMC of melanoma patients. The number of Treg, as measured by FOXP3 TSDR qPCR (left) and by FOXP3 protein FACS analysis (right), was determined prior to and 3 weeks after IL2 therapy. Both types of measurements were conducted on the same patients at the same time points.

FIG. 4 shows the FOXP3 DNA demethylation in patients presenting with different tumors. A) The box plots visualize the distribution of FOXP3 non-methylation levels grouped by patient diagnosis. Vertical axis is percent non-methylation. Individual box plots show the middle 50% of the data, the middle line is the median, whiskers extend to the most extreme data point which is no more than 1.5 times the inter-quartile range from the box. Grey points are individual measurement values. Patient numbers for the respective groups are given above the box plots. B) Receiver operating characteristic (ROC) curves. The ROC curves are plotted for the discriminations between normal and colorectal cancer (left panel) and lung cancer (right panel) patients.

FIG. 5 shows the FOXP3 non-methylation in patients presenting with different tumors. A) The box plots visualize the distribution of FOXP3 non-methylation levels grouped by patient diagnosis and gender. Vertical axis is percent non-methylation. Individual box plots show the middle 50% of the data, the middle line is the median, whiskers extend to the most extreme data point which is no more than 1.5 times the interquartile range from the box. Grey points are individual measurement values. Patient numbers for the respective groups are given above the box plots.

FIG. 7 shows the sequence of the TSDR of FoxP3 (SEQ ID NO:1), as well as the sequences of primers and probes (SEQ ID NOs:14-19) useful according to the present invention.

Figure 1:
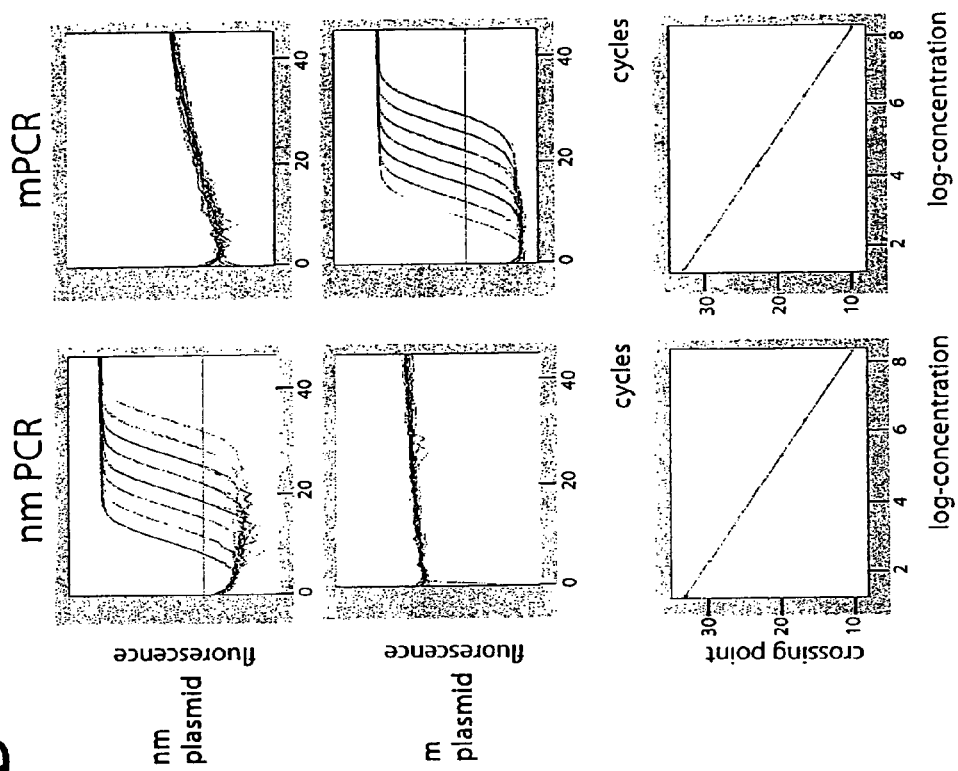
Figure 1:
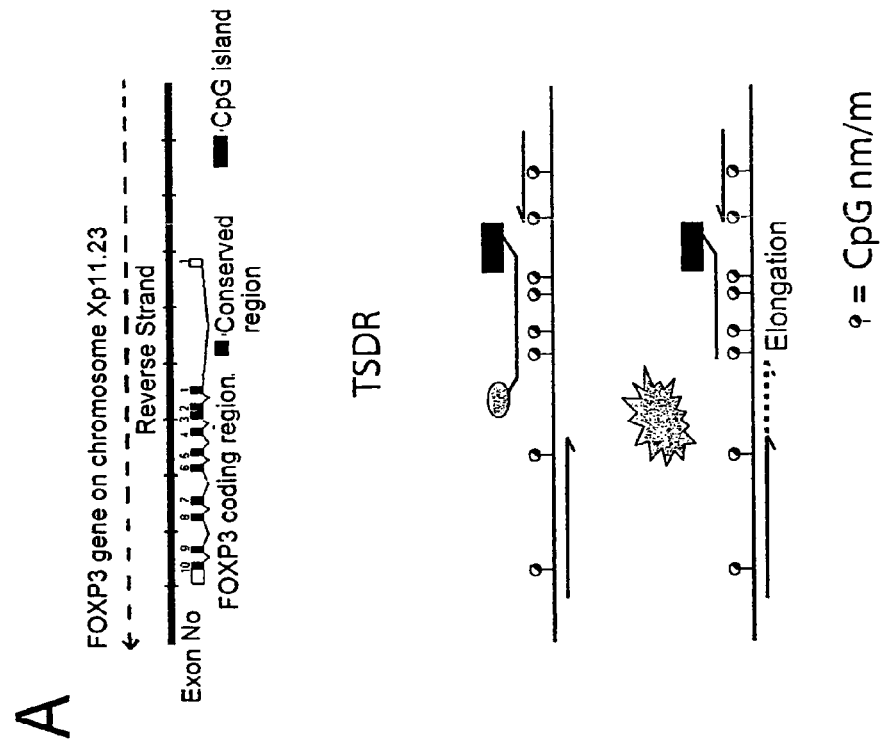

Seq ID No 1 shows the sequence of the TSDR of FoxP3.

Seq ID No 2 to 19 show the sequences of primers and probes as used in the examples.

Oligonucleotides

Sequences are given in 5' to 3' direction. Primers were used for bisulfite-specific PCR and sequence reactions. Strand specificity and orientation: Primers "p" and "o" produce amplicons based on the +1 strand, Primers "p" indicate forward, primers "o" denote reverse orientation.

```
                                         (SEQ ID No. 12)
p-TGTTTGGGGGTAGAGGATTT
                                         (SEQ ID. No. 13)
o-TATCACCCCACCTAAACCAA (SEQ ID No. 14)
p-methylated GTTTTCGATTTGTTTAGATTTTTTCGTT
                                         (SEQ ID No. 15)
p-non-methylated GTTTTtGATTTGTTTAGATTTTTTtGTT (SEQ ID No. 16)
o-methylated CCTCTTCTCTTCCTCCGTAATATCG
                                         (SEQ ID No. 17)
o-non-methylated CCTCTTCTCTTCCTCCATAATATCA
```

Probes

```
non-methylated 776_209-222_nm
                                         (SEQ ID No. 18)
ATGGTGGTTGGATGTGTTGGGTT methylated 776_209-222_m
                                         (SEQ ID No. 19)
ATGGCGGTCGGATGCGTC
```

EXAMPLES

Over the last decade, regulatory T cells have become a central focus of immunological research and in their coattails an important player in tumor immunity. Progress in understanding and medically exploiting this cell type remained difficult though. This mostly owes to the lack of specificity of FOXP3 and CD25 mRNA and protein markers. Both markers are also expressed by activated conventional T cells, and thus a distinction between those and true Treg was not possible. In contrast, all evidence from the inventors' previous studies (Baron et al., Floess et al.) suggest that demethylation of the FOXP3 TSDR is exclusive to a stable Treg phenotype and does not occur in transiently FOXP3 expressing activated T cells. Thereby, methylation analysis offers a clear advantage compared to the analysis of gene expression and protein synthesis.

The inventors argue that a precise identification of Treg is necessary to dissect their reported higher abundance in the peripheral blood of cancer patients. As yet, it could not be excluded that transiently FOXP3 expressing activated T cells contribute significantly to the measured FOXP3+ cell fraction. As a consequence, it was not finally established if Treg are indeed elevated in the peripheral blood of cancer patients or in cytokine therapies. However assuming the latter, the undefined intermixture lead to analytical fuzziness and thereby so far prevented that Treg counting could be used as an efficient monitoring and not at all as diagnostic tool. The inventors' qPCR assay is aimed at dispelling the aforementioned analytical fuzziness.

The inventors confirmed the specificity of TSDR demethylation to Treg when compared to all other major constituents of the immune system. In B-cells a residual demethylation of 1-2% was found. This may be a contamination due to the separation procedure where B-cells are initially sorted from PBMC by magnetic separation and some Treg may have unspecifically bound to the separation column, which has no impact on assay specifications. Another explanation would be a 1-2% B-cell fraction with demethylated FOXP3 TSDR. However, since only app. 1% of all blood leukocytes are B-cells, this would cause a negligible B-cell induced variation of app. 0.001-0.002% of FOXP3 levels in whole blood.

With the leukocyte fraction purified and sorted with $CD25^{++}$ $FOXP3^+$ antibodies, the inventors' assay reports 93% demethylation in male donors. The remaining 7% methylated cell fraction likely consists of $CD25^+$ $FOXP3^+$ cells that only transiently express FOXP3, without actually constituting stable Treg, fractions of CD25− and FOXP3− cells. Analysis of sorted naïve and memory CD4+ T cells confirms the assumption that app. 5-10% of $CD4^+$ T cells are Treg as found by demethylation of FOXP3 TSDR. Experimentally, this was controlled by the fact that depletion of the $CD25^{++}$ fraction from all $CD4^+$ cells yields a fully methylated cell pool. For female donors, the inventors saw 46% demethylation in the purified $CD25^{++}$ $FOXP3^+$ cell fraction, consistent with full methylation of the inactivated X-chromosome.

Testing potential routine application, the clinical significance and feasibility of the assay, the inventors measured blood samples from melanoma patients that were selected for an IL-2 treatment regimen. Previous observations suggested a significant increase of Treg upon IL-2 treatment. These observations ignited a debate as to whether this treatment would be beneficial (due to enhancement of NK and T effector cells) or adversarial (due to enhancement of the immune suppressive activity of Treg) to cure. In addition, a general activation of T cells transiently expressing FOXP3 and high levels of CD25 could not be ruled out with FACS analysis. Based on the fact that activated T cells do not show a decrease in methylation of the TSDR (Baron et al., 2007), the inventors' data provide strong support for the notion that the increasing number of cells with demethylated FOXP3 TSDR in course of IL-2 therapy really constitutes functional Treg rather than CD25 effector T-cells, confirming concerns that IL-2 therapy stimulates immunosuppressive Treg. Clinically, this data set must be further evaluated and final conclusions drawn independently. However, it may now be an option to reanalyze Treg levels of melanoma patients that received IL-2 therapy in an attempt to stratify patient cohorts in an attempt to personalize IL-2 therapy for its use in smaller but possibly more responsive populations.

In addition to these results, the inventors found significantly lower inter-patient variances in qPCR than in FACS analysis that are likely consequence of a more defined biological or technical system. This result is in agreement with the assumption that FOXP3 demethylation is a singularity of Treg, while $CD25^{++}FOXP3^+$ protein or mRNA count is a combination of Treg and general T cell activation.

Encouraged by these findings, the inventors investigated the idea that FOXP3 TSDR demethylation assay might provide a new method for early detection of solid tumors.

For this purpose, a blinded study was conducted that included patients with four different tumor types, breast, prostate, colon and lung, and healthy donors retesting the raising, but avoiding previous experimental ambiguity, that measuring Treg in the peripheral blood could become an important parameter of cancer screening. In line with recent reports (Meloni 2006; Miller et al. 2006), it was shown that in blood from lung and prostate cancer patients significant higher signals of demethylated TSDR were found than in healthy controls. In contrast to reported increased numbers of CD4+ Treg in peripheral blood of colon cancer patients (Clark et al. 2006; Ling et al. 2007), no differences were found here when analyzing TSDR demethylation. For breast cancer patients the Treg number determined by the demethylation assay was scarcely non-significant but still distinctly higher than in controls. Analysis of a higher number of patients and controls may clarify significance for breast cancer and approve those for lung and prostate cancer. Notably, AUC values for three cancers at above 0.7 in the ROC curves are promising for application FOXP3 demethylation as early detection marker (LoftonDay et al., 2007). In the inventors' view, two conclusions can be drawn from the inventors' results: i) This study is the final call for monitoring Treg levels as parameter for malignant developments in the body. ii) Extensive further studies are required for the various cancer indications, in order to validate TSDR demethylation as a marker for each malignancy.

The inventors' findings—if furthered and fully established—render measurement of regulatory T cell number by analysis of the FOXP3 TSDR a prime target not only for early tumor recognition but also for anti-tumor strategies. The general properties of DNA methylation, the assay specifications, and the biological properties of FOXP3 TSDR demethylation suggest that analysis of Treg counts is possible from app. 10 µl non-separated, snap-frozen blood. Compared to FACS analyses monitoring Treg number via methylation specific qPCR would greatly simplify analysis of large sample cohorts and screening in multicenter studies. This straightforward detection method of Treg number now ought to be included in all cancer vaccine studies, since Treg is the natural opponent of cancer vaccines. Patient stratifications should be adjusted to Treg levels. Also, more general clinical monitoring as exemplified in the described IL-2 study requires the analysis of Treg counts. This is in particular so for novel cytokine based medications such as IL-7, IL12 therapies. With the assay presented in here, this should be possible even in retrospective analysis, in case stored DNA or blood samples are available.

Here, the inventors established a quantitative PCR-based methylation assay, which is able to specifically and sensitively detect Treg, i.e. demethylated FOXP3 DNA, in all tested tissues and largely independent of sample amount and quality. The inventors then addressed the question as to whether this tool reliably reports Treg numbers in in vivo applications, using blood from melanoma patients before and after receiving IL2 cytokine treatment, which was previously and with other technologies shown to induce an elevation of Treg in the peripheral blood. With the validity of the assay proven the inventors conducted a fully blinded study testing the ability of FOXP3 TSDR demethylation in the blood stream to predict the presence of malignancies in the body.

Example I

Materials and Methods

Samples, Sample Preparation—Healthy Donors

Peripheral blood samples were obtained from healthy donors after informed consent in accordance with local ethical committee approval. For the sorting of major peripheral blood leukocyte populations, samples were treated according to Baron et al. EJI 2007). For CD4 sorting, peripheral blood mononuclear cells (PBMC) were isolated by density gradient centrifugation using Ficoll-Hypaque (Sigma-Aldrich). CD4+ T cells were isolated from buffy-coat-derived PBMCs by using anti-CD4 microbeads and the AutoMACS magnetic separation system (Miltenyi Biotec). All antibodies for cell surface stainings were from BD Pharmingen. The PE anti-human FOXP3 staining set was from eBioscience. All microbeads were purchased from Miltenyi Biotec. MACS-sorted CD4+ T cells were stained using anti-CD45RA-FITC and anti-CD25-APC. Cells were sorted into CD25highCD45RA− Tregs and CD25−CD45RA+ naïve T cells by FACS (Aria, BD-Bioscience). An aliquot of the CD4 population was used to determine the content of FOXP3+ cells by flow cytometry; here, the analyzing gates resemble the sorting gates. Cytometric analysis was performed as previously described (Huehn, J., Siegmund, K., Lehmann, J., Siewert, C., Haubold, U., Feuerer, M., Debes, G. F., Lauber, J., Frey, O., Przybylski, G. K., Niesner, U., Rosa, M. d. l., Schmidt, C. A., Bräuer, R., Buer, J., Scheffold, A. and Hamann, A., Developmental stage, phenotype and migration distinguish naive- and effector/memory-like CD4+ regulatory T cells. J Exp Med 2004. 199: 303-313) using a FACS Calibur (BD Biosciences) and the FlowJo software (Tree Star). Intracellular FOXP3 staining was performed with the PE anti-human FOXP3 staining set (eBioscience) according to the manufacturers instructions.

Samples, Sample Preparation—IL-2 Therapy Melanoma Patients

Melanoma patients had stage 1V metastatic disease and had received three different IL-2-based treatment regimens either by subcutaneous administration with or without addition of histamine dihydrochloride or intravenous decrescendo IL-2 over five days together with IFN-a (Asemissen A M, Scheibenbogen C, Helistrand K, Thoren F, Gehlsen K, Lesch A, Thiel E, Keilholz U. Addition of histamine to IL-2 treatment augments type 1 T cell responses in melanoma patients in vivo: immunological results from a randomized clinical trial of IL-2 with or without histamine. Clinical Cancer Res 11, 290-297, 2005; and Keilholz U, Goey S H, Punt C J A, Proebstle T, Salzmann R, Scheibenbogen C, Schadendorf D, Lienard D, Hantich B, Geueke A-M, Eggermont A M M. IFNβ/IL-2 with or without Cisplatinum in metastatic melanoma: a randomized trial of the EORTC melanoma cooperative group. J Clin Oncology, 2579-2588, 1997). After informed consent, heparinized blood samples were drawn before and 2 weeks after IL-2 therapy and peripheral blood mononuclear cells (PBMC) were isolated by density gradient centrifugation using Ficoll-Hypaque 1.077 (Biochrom, Berlin, Germany or Sigma-Aldrich), and stored in liquid nitrogen. For extracellular staining the following surface mAbs were used: anti-CD3-PercP (clone SK7), anti-CD25-PE (M-A251), anti-CD4-FITC (B9.11). Nuclear Anti-FOXP3-APC staining was performed according to the manufacturer's instructions using anti-FOXP3-APC (PCH101) (eBioscience, San Diego, USA). Data acquisition was performed on FACSCalibur (BD Bioscience).

Samples, Sample Preparation—Blinded Study

Blood was collected in one or more 10 ml BD vacutainer tube (BD Vacutainer® Plus blood Collection tube, BD 366643 16 mm×100 mm, 10.0 ml, K2 EDTA) and each tube immediately inverted ~10× to avoid blood clotting. The blood collection tubes were centrifuged at 1500 g for 10 minutes at 4° C. with the centrifuge brake turned off. After centrifugation about 0.5-1 ml of fluid including the cellular layer between plasma and erythrocytes were transferred into a pre-labeled 2 ml Cryo vial (Fisherbrand 2-ml Round-Style Bottom Cryogenic Storage Vials (Fisher Scientific #12-567-501)) using a single use pipette (Jumbo Bulb Pipette VWR #100500-622). Samples were frozen at −70/80° C. within 4 h of the blood draw and stored at this temperature until shipped on dry ice.

Methylation Analyses Protocol

Focusing on a 30.8 kb region of the sf locus (Brunkow M E et al (2001) Nat Gen. 27:68) harboring the foxp3 gene, sequences for methylation analysis was selected based on the CpG density. In particular, promoter regions as well as exon intron borders were considered for amplicon design. Upon PCR, primers were designed to analyze the TSDR region.

Genomic DNA was isolated from purified lymphocytes using the DNeasy tissue kit (Qiagen, Hilden, Germany) following the supplier's recommendations.

Sodium bisulfite treatment of genomic DNA was performed according to Olek et al. (Olek, A., Oswald, J., Walter, J. (1996) *Nucleic Acids Res.* 24, 5064-5066) with minor modifications, resulting in the conversion of unmethylated cytosine to uracil, whereas methylated cytosines remain unchanged. In a subsequent PCR amplification uracil is replaced by thymine. Thus, detection of a "C" in sequencing reactions reflects methylation of the genomic DNA at that site. Detection of a "T" at the same site instead, reflects the absence of a methyl modification of the genomic cytosine.

PCRs were performed on MJ Research thermocyclers (Waltham, Mass., United States) in a final volume of 25 μl containing 1×PCR Buffer, 1 U Taq DNA polymerase (Qiagen, Hilden, Germany), 200 μM dNTPs, 12.5 pmol each of forward and reverse primers, and 7 ng of bisulfite-treated genomic DNA. The amplification conditions were 95° C. for 15 min and 40 cycles of 95° C. for 1 min., 55° C. for 45 sec and 72° C. for 1 min. and a final extension step of 10 min. at 72° C. PCR products were purified using ExoSAP-IT (USB Corp., Cleveland, Ohio, United States) and sequenced applying the PCR primer(s) and the ABI Big Dye Terminator v1.1 cycle sequencing chemistry (Applied Biosystems, Foster City, Calif., United States) followed by capillary electrophoresis on an ABI 3100 genetic analyzer. Trace files were interpreted using ESME, which normalizes sequence traces, corrects for incomplete bisulfite conversion and allows for quantification of methylation signals (Lewin, J., Schmitt, A. O., Adorjan, P., Hildmann, T., Piepenbrock, C. (2004) Bioinformatics. 20, 3005-3012).

Results

In order to verify the suggested specificity of FOXP3 TSDR demethylation to Treg, the inventors established a quantitative real time-PCR system (qPCR). This system consists of methylation dependent primers and hybridization probes for both bisulphite converted methylated and bisulphite converted unmethylated DNA of the FOXP3 TSDR (FIG. 1a). Testing this system the inventors showed high specificity and no cross reactivity with the opposite species, even at unphysiologically high concentration (200 million copies of plasmid DNA) (FIG. 1b). Detection was possible with an absolute sensitivity down to a single DNA copy and a relative sensitivity of a minimum of 2.5 unmethylated in 10000 methylated copies (data not shown).

Figure 2:
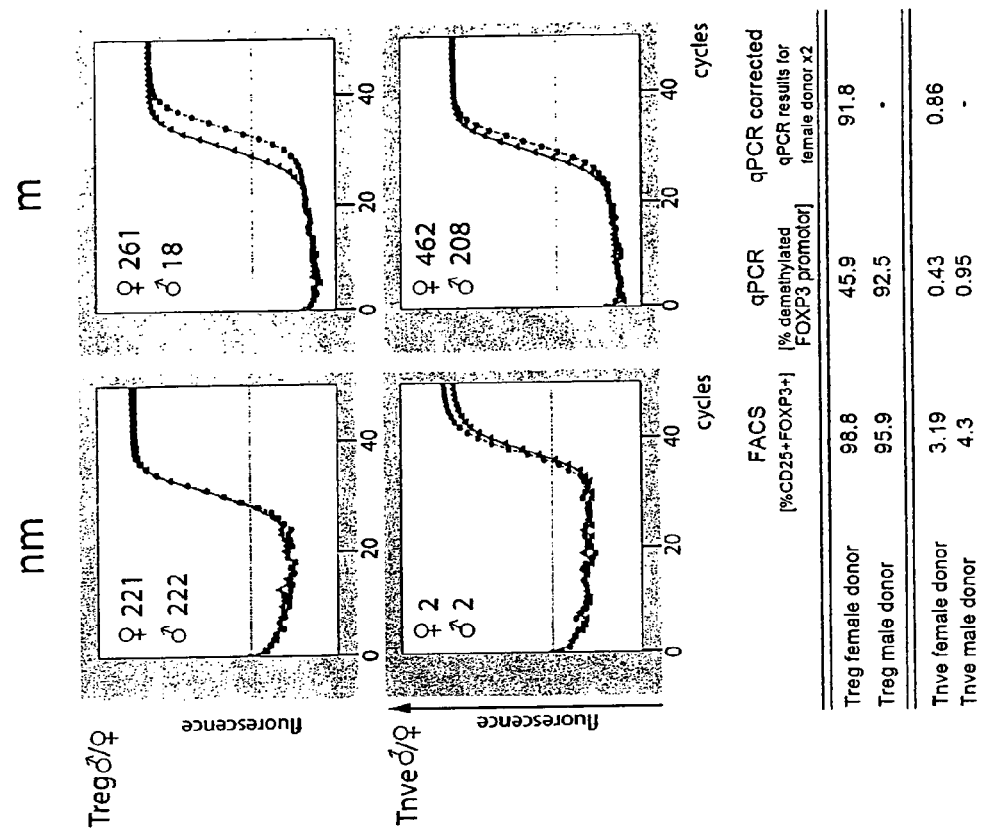
Figure 2:
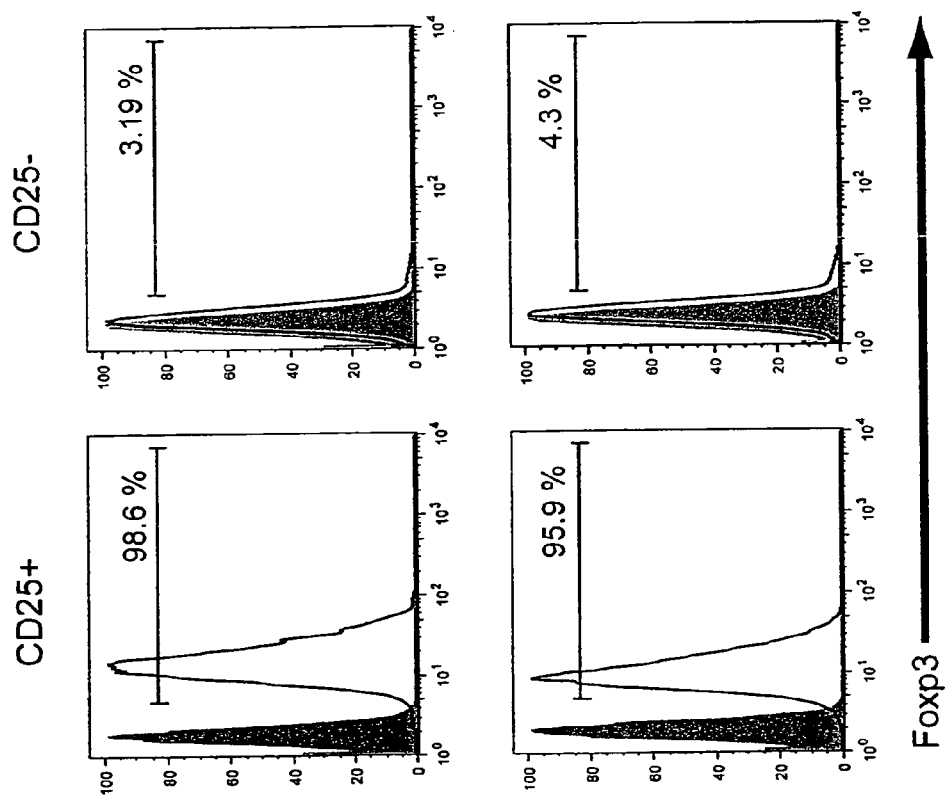

With technical parameters specified, the inventors compared demethylation data at the FOXP3 TSDR with FOXP3 protein staining in sorted CD25$^{++}$ T cells from male and female donors (FIG. 2). To control for biological specificity the inventors used CD25$^+$ depleted CD4$^+$ T cells (CD25−). The data show that FOXP3 staining of CD25$^{++}$ cells yields app. 95% of FOXP3$^+$ cells. Methylation analysis confirms these findings with app. 93% of the CD25$^+$ cells showing an unmethylated FOXP3 promoter in male donors and 45.9% in female donors (app. 92% of the cells, when corrected with a factor 2 owing to x-inactivation). In FACS analysis, 3-4% of CD25-cells appear to be FOXP3$^+$, while less than 1% of cells are demethylated in the FOXP3 TSDR. Thus, and in principle, demethylation of FOXP3 goes along with what is measured by FACS-analysis.

FOXP3 qPCR Methylation Assay in Blood Cell Subtypes

Next and in order to elicit the feasibility of Treg counting by means of FOXP3 demethylation in whole blood, the inventors tested the methylation level of various leukocyte fractions. The inventors show that isolated CD15$^+$ granulocyte, CD14$^+$ monocyte, CD58$^+$ natural killer cell and both CD8$^+$ memory (CD27$^+$CD45RA$^+$) and CD8$^+$ naïve (CD27$^+$CD45RA$^-$) cytotoxic T cell fraction showed only residual demethylation of less than 1% of the DNA at this locus. CD19$^+$ memory and naïB cell fractions comprise less than 2% demethylated FOXP3 promoter (Table 1). It is unclear if this fraction was owed to incomplete purification or to a naturally occurring B-cell subfraction with demethylated FOXP3.

CD4$^+$CD27$^+$CD45RA$^+$ naïve T cells showed a demethylated fraction of 6.2% and CD4$^+$CD27$^+$CD45RA$^-$ memory T cells showed a proportion of demethylated FOXP3 of 10.86%. Both fractions have been described as containing app. 10% of CD25$^{++}$FOXP3$^+$ regulatory T cells and were therefore expected to contain demethylated DNA at that order of magnitude. Selective depletion of the CD25$^{++}$ cells from the total CD4$^+$ T cell fraction removed almost entirely the demethylated FOXP3 TSDR portion.

TABLE 1

Methylation levels in major leukocyte cell types as determined by qPCR.

| Blood cell types | qPCR result [% demethylated FOXP3 promotor] |
|---|---|
| CD4$^+$CD27$^+$CD45RA$^+$ naive T-cells | 6.2 |
| CD4$^+$CD27$^+$CD45RA$^-$ memory T-cells | 10.86 |
| CD8$^+$CD27$^+$CD45RA$^+$ naive cytotoxic T-cells | 0.49 |
| CD8$^+$CD27$^+$CD45RA$^-$ memory cytotoxic T-cells | 0.34 |
| CD15$^+$ granulocytes | 0.01 |
| CD14$^+$ monocytes | 0.06 |
| CD56$^+$ NK-cells | 0.07 |
| CD19$^+$ naive B-cells | 1.96 |
| CD19$^+$ memory B-cells | 1.34 |

FOXP3 DNA Demethylation in Melanoma Patients with IL2 Therapy

Figure 3:
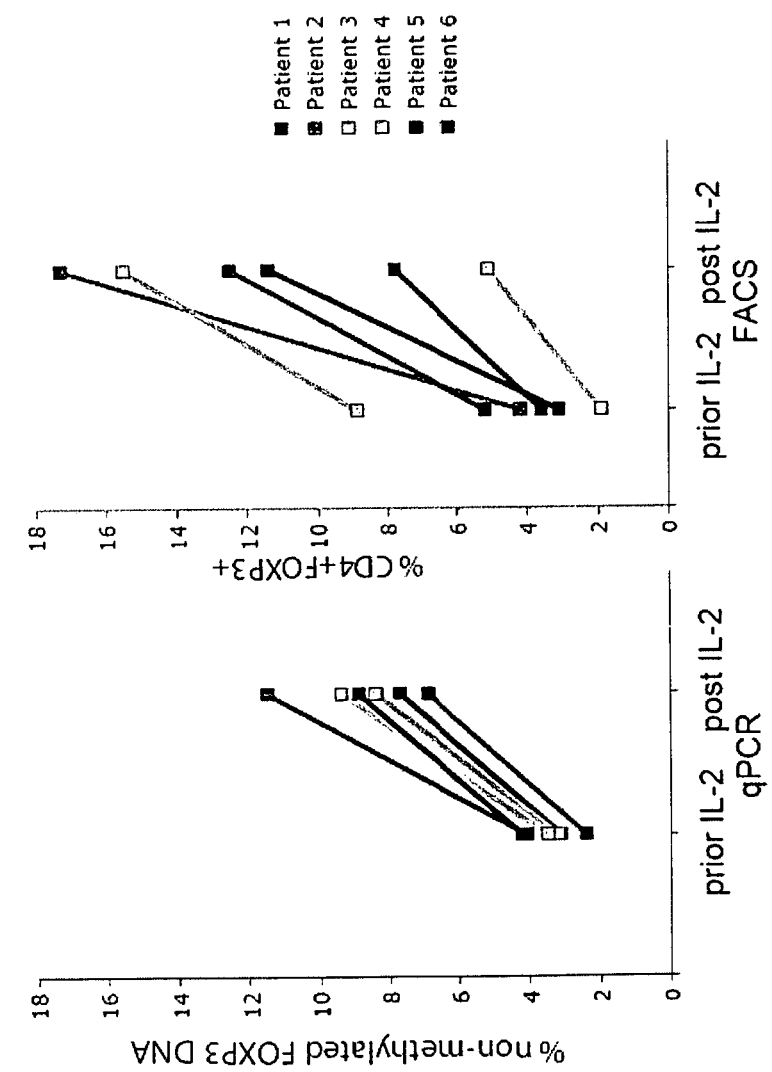

All isolated leukocyte fractions from peripheral blood, other than CD25$^{++}$ FOXP3$^+$ Treg, are entirely methylated in ex vivo experiments. Thus, identification and quantification of the cell fraction that is equivalent with stably FOXP3 expressing Treg is possible from whole blood samples by detecting the demethylated DNA applying the inventors' qPCR assay. To analyse Treg levels via DNA methylation in peripheral blood as reporter for immunmodulating therapies, the inventors tested the validity of the assay in a clinically applied cytokine cancer therapy. For this, the inventors chose IL-2 therapy, which is employed to achieve activation of cytotoxic T and NK cells. More recently, studies have shown that Foxp3$^+$ T cells are also enhanced by that therapy. The latter effect is contraindicated, as the therapy serves to stimulate the immune system, rather than suppressing it. However, FACS analysis of CD25++ and FOXP3+ cells can not rule out measurement of activated T cells without regulatory character. The inventors analyzed the impact of IL-2 therapy on the frequency of CD4$^+$CD25$^{++}$Foxp3$^+$ Treg in the peripheral blood of 6 patients with metastatic melanoma both by methylation and FACS analysis (FIG. 3). Patients had received three different IL-2-based therapy regimens either IL-2 as prolonged subcutaneous administration with or without addition of histamine dihydrochloride or intravenous decrescendo IL-2 over five days with IFN-alpha. Prior to therapy, FACS measurements showed an average level of CD4$^+$CD25$^{++}$Foxp3$^+$ Treg of 4.5% in PBMC ranging from 1.9 to 8.9% and a standard deviation of 2.4%. When the Treg count was determined by qPCR, the average level of FOXP3 TSDR demethylation was at 3.4% ranging from 2.4 to 4.2% with a standard deviation of 0.7%. Average FOXP3 levels after IL-2 therapy were found to be 11.6% ranging from 5.1 to 17.3% with a standard deviation of 4.6% when measured by FACS, translating into a 1.7-4.1 fold increase of Treg after therapy. When determined by demethylation of FOXP3 TSDR, the average Treg number was at 8.8% ranging from 6.9 to 11.5% with a standard deviation of 1.6%, translating into a 2.1 to 2.8 fold increase after therapy. Treg number estimates from the two techniques are well correlated (Pearson correlation R=0.65, P=0.023), and both suggest app. a 2-fold increase of Treg upon IL2 treatment. The low inter-patient variance observed in this study for FOXP3 demethylation in whole blood samples reconfirmed the possibility that such an assay might reduce the variances when determining Treg in blood samples of cancer patients, while retaining the previously reported increase of Treg in cancer patients compared to healthy individuals.

FOXP3 DNA Demethylation in Cancer Patients

Figure 4:
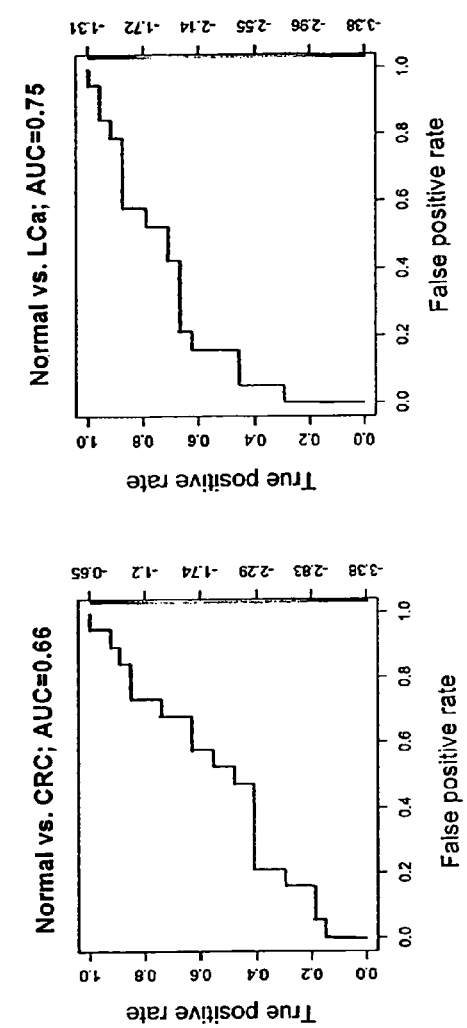
Figure 4:
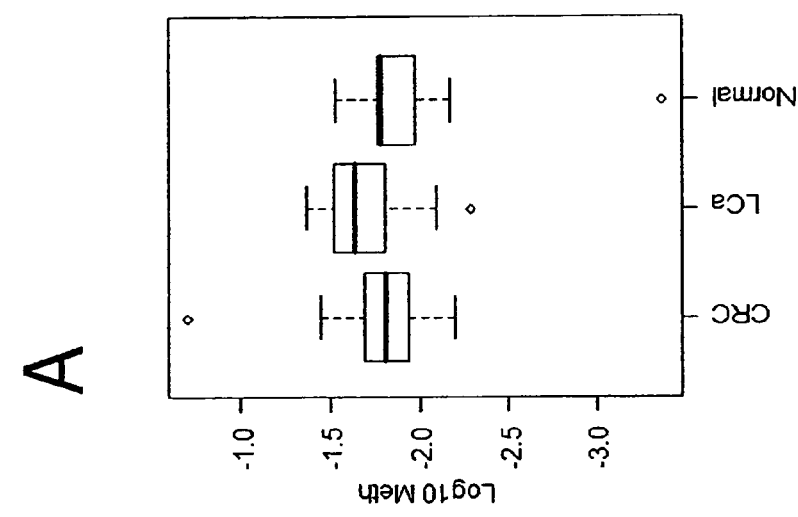

The inventors measured the methylation status of the FOXP3 TSDR in a total of 115 frozen "buffy coats" from healthy controls, colorectal, lung, prostate and breast cancer patients in a fully blinded study. Since FOXP3 is X-linked, demethylation for female donors was corrected by a factor 2 in order to report the Treg number. For healthy donors, the average Treg count was at 1.4% ranging from 0.4 to 2.9%. For colorectal cancer patients the Treg number was at 2.3%, ranging from 0.6 to 3.5 with one unexpected outlier at 19%. Excluding the outlier, the average Treg count was at 1.64%, only slightly higher than healthy donors. Treg number in lung cancer patients ranged from 0.5 to 4.4% with an average of 2.3%. While results for colorectal cancer patients did not significantly differ from normal controls, Treg number in lung cancer patients is significantly elevated (p=0.003). Among the samples obtained from early stage lung tumors (stage I and II, see supplementary information), 6 out of 9 were found to have significantly elevated Treg counts. Receiver operating characteristics (ROC) curves for colon and lung cancer show an AUC (area under curve) of 0.66 for colon and an AUC of 0.75 for lung cancer (FIG. 4, FIG. 5c).

Figure 5:
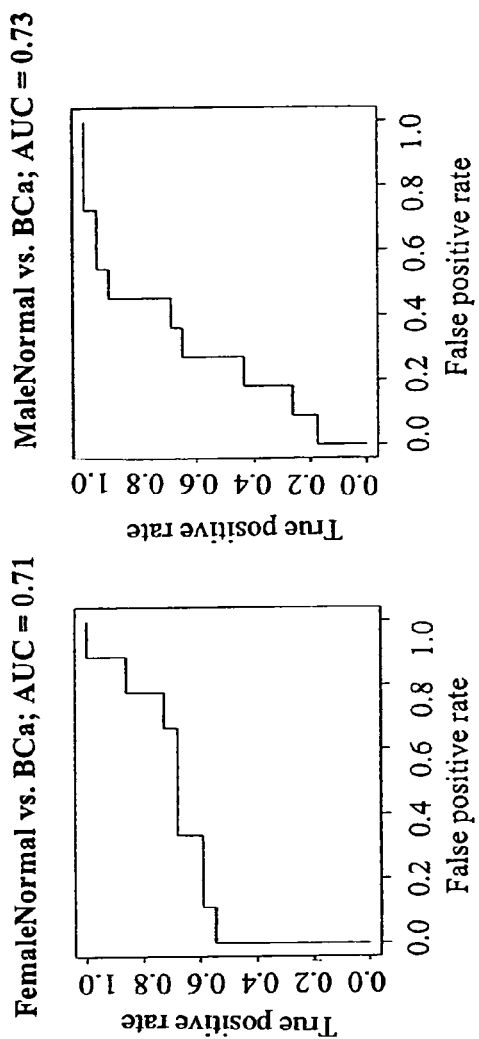
Figure 5:
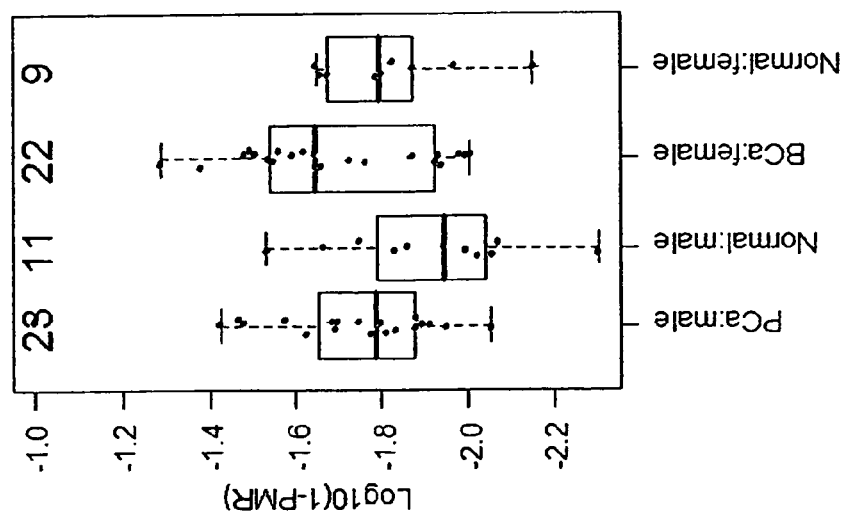
Figure 6:
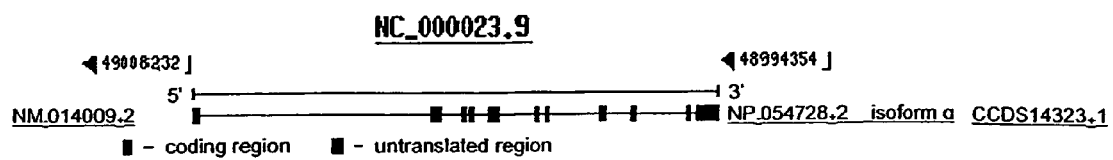
FIG. 6 shows the genetic organization of the human foxp3 gene in Accession Number NC_000023.

When comparing Treg count in breast and prostate cancer patients to healthy sex-matched controls, the average Treg count was elevated to 2.4% and 2.4%, respectively, compared to 1.7 and 1.4% in normal controls. The changes compared to normal individuals were statistically significant for prostate cancer with p=0.03 and slightly below significance for breast cancer with p=0.08, respectively. ROC curves for both breast and prostate cancer show an AUC of 0.71 for breast cancer and an AUC for prostate cancer of 0.73 (FIG. 5).

Example II

Samples, Sample Preparation—Healthy Donors

Peripheral blood samples were obtained from healthy donors after informed consent in accordance with local ethical committee approval. For the sorting of major peripheral blood leukocyte populations, samples were treated according to Baron et al. (36). For CD4+ T cell sorting, peripheral blood mononuclear cells (PBMC) were isolated by density gradient centrifugation using Ficoll-Hypaque (Sigma-Aldrich, Munich, Germany). CD4+ T cells were isolated from buffy-coat-derived PBMCs by using anti-CD4 microbeads and the AutoMACS magnetic separation system (Miltenyi Biotec, Bergisch Gladbach, Germany). All microbeads were purchased from Miltenyi Biotec and all antibodies for cell surface stainings were from BD Pharmingen (Heidelberg, Germany). Intracellular FOXP3 staining was performed with the PE anti-human FOXP3 staining set (eBioscience, San Diego, USA) according to the manufacturers instructions. MACS-sorted CD4+ T cells were stained using anti-CD45RAFITC and anti-CD25-APC. Cells were sorted into CD25highCD45RA− Treg and CD25−CD45RA+naïve T cells by FACS (Aria, BD-Bioscience, Heidelberg, Germany). An aliquot of the CD4 population was used to determine the content of FOXP3+ cells by flow cytometry; here, the analyzing gates resemble the sorting gates. Cytometric analysis was performed as previously described (50) using a FACS Calibur (BD Biosciences) and the FlowJo software (Tree Star, Ashland, Oreg., USA).

Samples, Sample Preparation—IL-2 Therapy Melanoma Patients

Melanoma patients had stage IV metastatic disease and had received IL-2 by subcutaneous administration with or without addition of histamine dihydrochloride as described previously. After informed consent, heparinized blood samples were drawn before and two weeks after IL-2 therapy and peripheral blood mononuclear cells (PBMC) were isolated by density gradient centrifugation using Ficoll-Hypaque 1.077 (Biochrom, Berlin, Germany or Sigma-Aldrich), and stored in liquid nitrogen. For extracellular staining the following surface mAbs were used: anti-CD3-PercP (clone SK7), anti-CD25-PE (M-A251), anti-CD4-FITC (B9.11). Nuclear Anti-FOXP3-APC staining was performed according to the manufacturer's instructions using anti-FOXP3-APC (PCH101) (eBioscience). Data acquisition was performed on FACS-Calibur (BD Bioscience).

Samples, Sample Preparation—Blinded Study

Blood was collected in one or more 10 ml BD vacutainer tube (BD Vacutainer® Plus blood Collection tube, BD 366643 16 mm×100 mm, 10.0 mL, K2 EDTA) and each tube immediately inverted ~10× to avoid blood clotting. The blood collection tubes were centrifuged at 1500 g for 10 minutes at 4° C. with the centrifuge brake turned off. After centrifugation about 0.5-1 ml of fluid including the cellular layer between plasma and erythrocytes were transferred into a pre-labeled 2 ml Cryo vial (Fisherbrand 2-mL Round-Style Bottom Cryogenic Storage Vials (Fisher Scientific, Schwerte, Germany, #12-567-501)) using a single use pipette (Jumbo Bulb Pipette VWR, Darmstadt, Germany, #100500-622). Samples were frozen at −70/80° C. within 4 h of the blood draw and stored at this temperature until shipped on dry ice. Written informed consent was obtained from all study participants adhering to the local ethical guidelines.

Sample Preparation FFPE-Samples

DNA isolation of up to eight slices from formalin-fixed, paraffin-embedded (FFPE) tissues derived from tumor as well as healthy tissue of colorectal cancer patients was performed with Qia-AMP DNA FFPE tissue kit (Qiagen, Hilden, Germany) according to manufacturers protocol. As modification prior to DNA isolation formalin released tissue was incubated over night in 50 mM Tris/HCl pH 8, 1 mM EDTA, 0.5% Tween 20 containing 2 mg/ml proteinase K with subsequent incubation at 90° C. for 10 min.

DNA Preparation and Bisulfate Conversion

Genomic DNA was isolated using the DNeasy blood and tissue kit (Qiagen, Hilden, Germany). For PBMC and sorted blood cells the protocol for cultured cells was followed, for DNA isolation from buffy coats the whole blood protocol was used. Bisulfite treatment of genomic DNA was performed according to Olek et al. (Olek, A., Oswald, J., Walter, J. 1996. A modified and improved method for bisulphite based cytosine methylation analysis. *Nucleic Acids Res.* 24: 5064-6) with minor modifications.

Realtime-PCR

Realtime-PCR was performed in a final reaction volume of 20 μl using Roche LightCycler® 480 Probes Master (Roche Diagnostics, Mannheim, Germany) containing 15 pmol each of methylation or non-methylation specific forward and reverse primers for TSDR (36), 5 pmol hydrolysis probe, 200 ng lambda-DNA (New England Biolabs, Frankfurt, Germany) and 30 ng bisulfite-treated genomic DNA template or respective amount of plasmid standard. Each sample was analyzed in triplicate using a Light-Cycler 480 System (Roche). Cycling conditions consisted of a 95° C. preheating step for 10 min and 50 cycles of 95° C. for 15 sec followed by 1 min at 61° C.

Plasmid-Standard

PCR-Products were generated with methyl- and non-methyl-specific primers for FOXP3 TSDR using genomic, bisulfit-treated DNA from sorted naive and regulatory T cells. DNA fragments were cloned into pCR2.1-TOPO vector, using TOPO TA Cloning® Kit (Invitrogen, Karlsruhe, Germany) according to manufacturers instructions and verified by sequencing. Plasmids were purified with Qiagen Plasmid Midi Kit, the concentration was determined by Qubit fluorometer (Invitrogen) and diluted to obtain final concentrations of 100, 10, 1 and 0.1 fg representing 20,000, 2,000, 200 and 20 plasmid copies as standard for qPCR reactions, each for methylated and non-methylated FOXP3 qPCR assay.

Statistical Analysis

Amounts of methylated and unmethylated FOXP3 DNA were estimated from calibration curves by linear regression on crossing points from the second-derivative maximum method. The median was used to aggregate triplicate measurements of the buffy coat samples. The proportion of unmethylated DNA was computed as the ratio of unmethylated FOXP3 TSDR-DNA and the sum of methylated and unmethylated FOXP3 TSDR-DNA. For female patients this ratio was multiplied with a factor of two. Areas under the ROC curves were estimated by means of the trapezoidal rule. The Wilcoxon rank-sum test was used to compare demethylation rates between normal and cancer patients. The Wilcoxon signed-rank test was used to compare demethylation rates pre- and post-IL-2 treatment. For correlation analysis Pearson's product moment coefficient and t-test statistic were used. All P values are 2-sided.

Immunohistochemistry

Immunohistochemical staining was performed as previously described. In brief, slides were incubated with the rat monoclonal antibody against human FOXP3 protein (PCH101, 1:200; eBioscience, San Diego, USA), followed by biotin-conjugated rabbit anti-rat and the EnVision peroxidase kit (Dako, Glostrup, Denmark). Ten randomly selected high power fields (1 HPF=0.237 mm$^2$) were analyzed for FOXP3$^+$ cell infiltration in tumor tissue and matched normal colonic mucosa/lung parenchyma, and 10 HPF were averaged in each case.

The invention claimed is:

1. A method for identifying FoxP3-positive CD25$^+$CD4$^+$ regulatory T cells (Tregs) of a human subject, the method comprising:

Isolating genomic DNA from a biological sample from the subject, and treating the genomic DNA with bisulfite, detecting, in the bisulfite treated genomic DNA, the methylation status of at least one CpG position in the region of the foxp3 gene consisting of SEQ ID NO: 1;

wherein said detecting the methylation status comprises creating an amplicon by amplification with at least one methylation-specific primer having the sequence of SEQ ID NO: 14 or 16, and at least one non-methylation-specific primer having the sequence of SEQ ID NO: 15 or 17, and hybridizing the resulting amplicon with at least one suitable methylation-specific probe and/or at least one suitable non-methylation-specific probe;

determining that said at least one CpG position is demethylated to at least 90%: and correlating the detected extent of demethylation of said at least one CpG position with an identification the sample as having FoxP3-positive CD25$^+$CD4$^+$ regulatory T cells.

2. The method according to claim 1, wherein said sample is selected from the group of whole blood, paraffin-embedded tissue, fractions of blood, tissue, solid tissue, cell or tissue cultures, body fluids, organs and other samples that are suspected of containing Tregs.

3. The method according to claim 1, wherein said determining the methylation status comprises a method selected from the group consisting of methylation specific enzymatic digests, promoter methylation analysis, CpG island methylation analysis, MSP, HeavyMethyl, MethyLight, PCR and/or real time PCR.

4. The method according to claim 1, wherein said determining the methylation status further comprises amplification with at least one primer of the primer pair SEQ ID NOs:4 and 5 before said amplification of said bisulfite treated genomic DNA with said at least one methylation-specific primer and said at least one non-methylation-specific primer.

5. The method according to claim 1, the method further comprising determining the amount of FoxP3-positive CD25$^+$CD4$^+$ regulatory T-cells present in said sample based on said methylation status.

6. The method according to claim 5, wherein said biological sample is a tissue, further comprising the step of determining the tissue status with respect to Treg infiltration and FoxP3 expression status of said tissue.

7. A method for diagnosing the immune status of a human, the method comprising the steps of:
  a) providing a sample containing T-cells from said human;
  b) determining the sample as having FoxP3-positive CD25+CD4$^+$ regulatory T cells using the method of claim 1;
  c) determining the amount of regulatory T-cells present in said sample based on said methylation status, and
  d) diagnosing the immune status of said human based on said amount as determined, wherein the extent of demethylation of said at least one CpG in one allele to at least 91% is determined and is indicative of a FoxP3-positive CD25+CD4+ regulatory T cell.

8. The method according to claim 7, wherein said sample is selected from the group of whole blood, paraffin-embedded tissue, fractions of blood, tissue, solid tissue, cell or tissue cultures, body fluids, organs and other samples that are suspected of containing Tregs.

9. The method according to claim 7, further comprising measuring and/or monitoring the amount of said regulatory T cells in response to chemical and/or biological substances that are suspected to modulate FoxP3 expression in the regulatory T cell, to modify the amounts of Tregs, or to modulate Treg expansion, Treg levels, Treg migration behavior, or Treg survival.

10. The method, according to claim 1, wherein the determined extent of demethylation is at least 92%.

11. The method, according to claim 7, wherein the determined extent of demethylation is at least 92%.

12. The method according to claim 1, wherein said suitable methylation-specific probe has the sequence of SEQ ID NO: 19 and wherein said suitable non-methylation-specific probe has the sequence of SEQ ID NO: 18.

* * * * *

UNITED STATES PATENT AND TRADEMARK OFFICE
CERTIFICATE OF CORRECTION

Page 1 of 1

PATENT NO. : 9,017,972 B2
APPLICATION NO. : 13/000502
DATED : April 28, 2015
INVENTOR(S) : Ivana Türbachova et al.

It is certified that error appears in the above-identified patent and that said Letters Patent is hereby corrected as shown below:

In the specification

Column 12
Line 53, "and CD25 cells" should read -- and CD25⁻ cells --.

Column 18
Line 34, "and naïB cell" should read -- and naïve B cell --.

In the claims

Column 27
Line 22, "Isolating" should read -- isolating --.

Column 27
Line 37, "identification the sample" should read -- identification of the sample --.

Column 28
Line 30, "CD25+CD4⁺" should read -- $CD25^+CD4^+$ --.

Column 28
Line 37, "CD25+CD4+" should read -- $CD25^+CD4^+$ --.

Signed and Sealed this
Twenty-ninth Day of December, 2015

Michelle K. Lee
*Director of the United States Patent and Trademark Office*